United States Patent [19]

Grinda

[11] Patent Number: 5,914,347
[45] Date of Patent: Jun. 22, 1999

[54] PROCESS FOR THE STABILISATION OF POLYUNSATURATED FATTY ACIDS AND THE USE OF SAID STABILISED PRODUCTS IN THERAPEUTICS AND COSMETOLOGY

[76] Inventor: Jean-Robert Grinda, 38/40 Blvd. Flandrin, Paris, France, 75016

[21] Appl. No.: 08/809,198

[22] PCT Filed: Jul. 17, 1995

[86] PCT No.: PCT/FR95/00949

§ 371 Date: Mar. 11, 1997

§ 102(e) Date: Mar. 11, 1997

[87] PCT Pub. No.: WO96/02488

PCT Pub. Date: Feb. 1, 1996

[30]  Foreign Application Priority Data

Jul. 15, 1994 [FR] France ..................................... 94 08810

[51] Int. Cl.⁶ ........................... A61K 31/20; A61K 31/22
[52] U.S. Cl. ............................................ 514/560; 514/549

[58] Field of Search ...................... 514/549, 560

[56]  References Cited

U.S. PATENT DOCUMENTS

| 2,827,452 | 3/1958 | Schlenk et al. | ........................ 260/209 |
| 3,450,821 | 6/1969 | Carstensen et al. | ..................... 424/318 |
| 4,897,421 | 1/1990 | Braquet | ................................. 514/557 |

*Primary Examiner*—Raymond Henley, III
*Attorney, Agent, or Firm*—Bierman, Muserlian and Lucas

[57]  ABSTRACT

A process for the stabilization of polyunsaturated fatty acids and their alkyl esters wherein the polyunsaturated fatty acids or its alkyl or glyceryl esters is dissolved in an organic solvent and a hydroxy alkyl cellulose or a solution thereof in an inert solvent is added to the resulting solution and the solution is a dispersion evaporated to dryness under a inert gas to form the preparation in powder form which is useful for pharmaceutical formulations or cosmetic formulations.

18 Claims, 4 Drawing Sheets

PROCESS FOR THE STABILISATION OF POLYUNSATURATED FATTY ACIDS AND THE USE OF SAID STABILISED PRODUCTS IN THERAPEUTICS AND COSMETOLOGY

The present invention relates to the field of pharmacy, more particularly to that of therapeutic chemistry and to that of dermato-cosmetology.

More particularly, it relates to a process for the stabilisation of polyunsaturated fatty acids with a view to reliable and prolonged therapeutic use.

Interest in polyunsaturated acids, especially α- or γ-linolenic acid (vitamin F) has been increasing for several years because of their special role in various biological syntheses. For this reason, it has been possible to regard polyunsaturated fatty acids of the 18:3 series and particularly of the 20:3 series as key precursors and intermediates in the formation of prostaglandins PGE1 following a series of enzymatic reactions due to specific desaturases and to elongases.

Interest in unsaturated fatty acids in dermatology and cosmetology has also been increasing because of their regenerative and anti-ageing properties for the epidermis. In this respect, the properties of polyunsaturated fatty acids depend not on a possible conversion to prostaglandins or prostacyclins, but on a direct effect.

The use of polyunsaturated fatty acids in therapeutics derives from their ability to be converted to prostaglandins, and more particularly $PGE_1$ which have an important mediating function in the regulation of arterial pressure, in the motor function, in promoting the contraction of smooth muscle and in preventing gastric ulcers.

The hopes of using these acids have not been realised, on the one hand because of their poor degree of assimilation but on the other hand, and above all, because polyunsaturated fatty acids are oxidised readily and rapidly under the action of light, peroxides and, in particular, atmospheric oxygen, leading to the formation of resins.

Consequently, polyunsaturated fatty acids such as linolenic acids, stearidonic acid, eicosapentaenoic acid or dihomo-γ-linolenic acid or the synthetic analogues thereof readily undergo oxidation, hydroxylation or peroxidation, leading to metabolites with little or no activity which the body rejects or excretes. This is particularly the case with dihomo-γ-linolenic acid (cis 8, cis 11, cis 14-eicosatrienoic acid), the synthetic analogues thereof and with arachidonic acid (cis 5, cis 8, cis 11, cis 14-eicosatetraenoic acid).

In view of the therapeutic use, it appeared necessary therefore to have a means of preventing the oxidation of said polyunsaturated fatty acids or their esters if it is desired to keep them chemically intact and above all if it is considered important to retain the possibility of their being metabolised in the body to prostaglandins and/or prostacyclins. Indeed, the hydroxylated or oxidised decomposition products are inactive because they are not resorbed in the digestive tract or because they can no longer be converted by enzymatic systems to higher fatty acid homologues.

The aim, therefore, was to find a method of stabilising polyunsaturated fatty acids or their esters which enables them to remain stable without auto-oxidation and thus to act as a prodrug for prostaglandins. It is known that γ-linolenic acid or α-linolenic acid are converted rapidly under the action of specific desaturases and of elongases to dihomo-γ-linolenic acid, stearidonic acid and then to prostaglandins PGE, the beneficial effects of which on gastric cytoprotection are well-known. It is important to keep this enzymatic transformation fully intact.

When applied topically, polyunsaturated fatty acids also play an important part in maintaining or restoring the youth of the integument; numerous patents have shown the advantage of cosmetic, dermatological and nutritional preparations of polyunsaturated fatty acids.

In particular, attention is drawn to numerous patents which are interesting in that they show the topical use of polyunsaturated fatty acids, more specifically: a patent to INDENA dated Jul. 27, 1987 entitled "Polyunsaturated acids having vasokinetic action and pharmaceutical and cosmetic formulations containing them". The author of the patent points out that the topical use of essential fatty acids causes, to his surprise, beneficial vasodilator and vasokinetic effects on the veins, arterioles and capillaries and consequently leads to better cutaneous trophism.

Moreover, it is known that essential fatty acids (in reality, oils containing methyl gamma-linolenate) have been used successfully in the treatment of atopic eczema in infants.

See for example:

a publication taken from the British Journal of Dermatology has the title "Changes in transepidermal water loss and the composition of epidermal lecithin after applications of pure fatty acid triglycerides to the skin of essential fatty acid-deficient rats". The transepidermal water loss which is characteristic of an EFA deficiency in rats is reduced by a topical preparation of polyunsaturated fatty acids.

an article which appeared in the Quotidien du Médecin No. 5142 illustrated the protection of the skin from the effects of radiotherapy by essential fatty acids.

This stabilisation was achieved according to the process of the invention by dissolving the polyunsaturated fatty acid or one of its lower alkyl esters in an organic solvent, preferably non-hydroxylated, then adding to this solution a (hydroxyalkyl) cellulose or adding said solution to a solution of hydroxyalkyl cellulose in an inert solvent, then evaporating the solution or dispersion thus obtained to dryness in a protective gas atmosphere. The unsaturated fatty acid is enclosed in the hydroxyalkyl cellulose and the powder thus obtained is highly stable towards atmospheric oxygen and light. This formulation is stable at ambient temperature. This powder may then be diluted by an inert vehicle or excipient in order to prepare a pharmaceutical form such as capsules, tablets, dragees or pills.

The weight ratio of unsaturated fatty acid/hydroxyalkyl cellulose may vary widely such as, for example, between 0.1% and 50%. This ratio will be preferably between 1% and 10% for oral forms and for topical forms.

The preparation may contain a polyunsaturated fatty acid but it may also contain equally advantageously a lower alkyl ester, such as a methyl, ethyl, propyl or glyceryl ester (mono-, di- or triglycerides).

The (hydroxyalkyl) celluloses thus used may include hydroxyethyl and hydroxypropyl cellulose. This term also includes (hydroxyalkyl) alkyl celluloses such as, in particular, hydroxypropyl methylcellulose.

The tests carried out have confirmed that the dispersion of polyunsaturated fatty acid in a hydroxyalkyl cellulose and, more particularly, in hydroxypropyl methylcellulose exhibited long-term stability over a period up to at least four years and that, as a consequence, one of the main obstacles to the use of said polyunsaturated fatty acids was thus eliminated. This appeared to be unexpected in so far as alkyl derivatives of cellulose such as methylcellulose and ethylcellulose lead only to partial protection.

The invention finds a particular and advantageous use in the stabilisation of semi-synthetic or synthetic analogues of dihomo-γ-linolenic acid (cis 8, cis 11, cis 14-eicosatrienoic acid) such as those described in the publications D. A. Van Dorp, Rec. Trav. Chim. 94 (1975) 247–276 and L. HELINGA et al., J. of the Royal Netherlands Chemical Society 94 (1975) 26–29, and in particular 19-methyl eicosatrienoic acid.

These analogues substituted in the 2, 3, 4, 5, 18 or 19 position were difficult to store and, consequently, it has not yet been possible to study them fully from a pharmacological angle because of their susceptibility to oxidation.

It seems that the insertion of a hydroxyalkyl cellulose between the particles of polyunsaturated fatty acid or their esters leads to the rapid and complete disappearance of susceptibility to oxidation.

The invention also relates to the preparation of new pharmaceutical compositions containing a polyunsaturated fatty acid incorporated in a glycosidic polymer, particularly in association or in mixture with an inert carrier or vehicle suitable for oral or topical administration.

In particular, it relates to new pharmaceutical compositions characterised in that they contain a polyunsaturated fatty acid or an alkyl ester thereof, adsorbed on a hydroxyalkyl cellulose, in association or in mixture with an inert, non-toxic, pharmaceutically acceptable carrier or vehicle.

More specifically, it relates to new pharmaceutical compositions characterised in that they contain a polyunsaturated fatty acid or an ester thereof adsorbed on a hydroxypropyl methylcellulose.

The preparations obtained according to the process of the invention are particularly suitable for preventing certain adverse effects resulting from the suppression of prostaglandin synthesis, or for treating or preventing, in particular, the ulcerogenic effects of anti-inflammatory agents. The level of activity is of the same order as that of semi-synthetic prostaglandins such as misoprostol but, without doubt, in conjunction with the gradual or limited formation of PGE with much less pronounced side-effects.

It is thus possible to re-establish, during the administration of non-steroidal anti-inflammatory agents, the synthesis of prostaglandins from natural or synthetic precursors using a metabolic route other than that of prostaglandin oxidases or synthetases.

The anti-inflammatory agents administered are either derivatives of salicylic acid such as aspirin, amides of o-acetoxybenzoic acid or derivatives of anthranilic acid such as niflumic acid or esters thereof, tolfenamic acid, mefenamic acid or flufenamic acid or esters thereof, indolyl acetic acids such as indomethacin, sermetacin or acemetacin; phenylpropionic acids such as ketoprofen, pirprofen or diclofenac or pyrazolones such as phenylbutazone or oxyphenylbutazone, and oxicams.

In this way, the administration of the combination according to the invention, in association with aspirin, diclofenac or piroxicam reduces appreciably the occurrence of side-effects in patients who remain under treatment with a non-steroidal anti-inflammatory agent.

For topical application, the compositions according to the invention are used in the form of creams, lotions, milks, fragrant or perfumed powders or, in a general manner, any usual cosmetic or dermatological presentation.

The compositions according to the invention also constitute a mode of administering precursors of prostaglandins, especially El, so these prostaglandins are able to express all their activity in particular in the various metabolisms.

Figure 1:
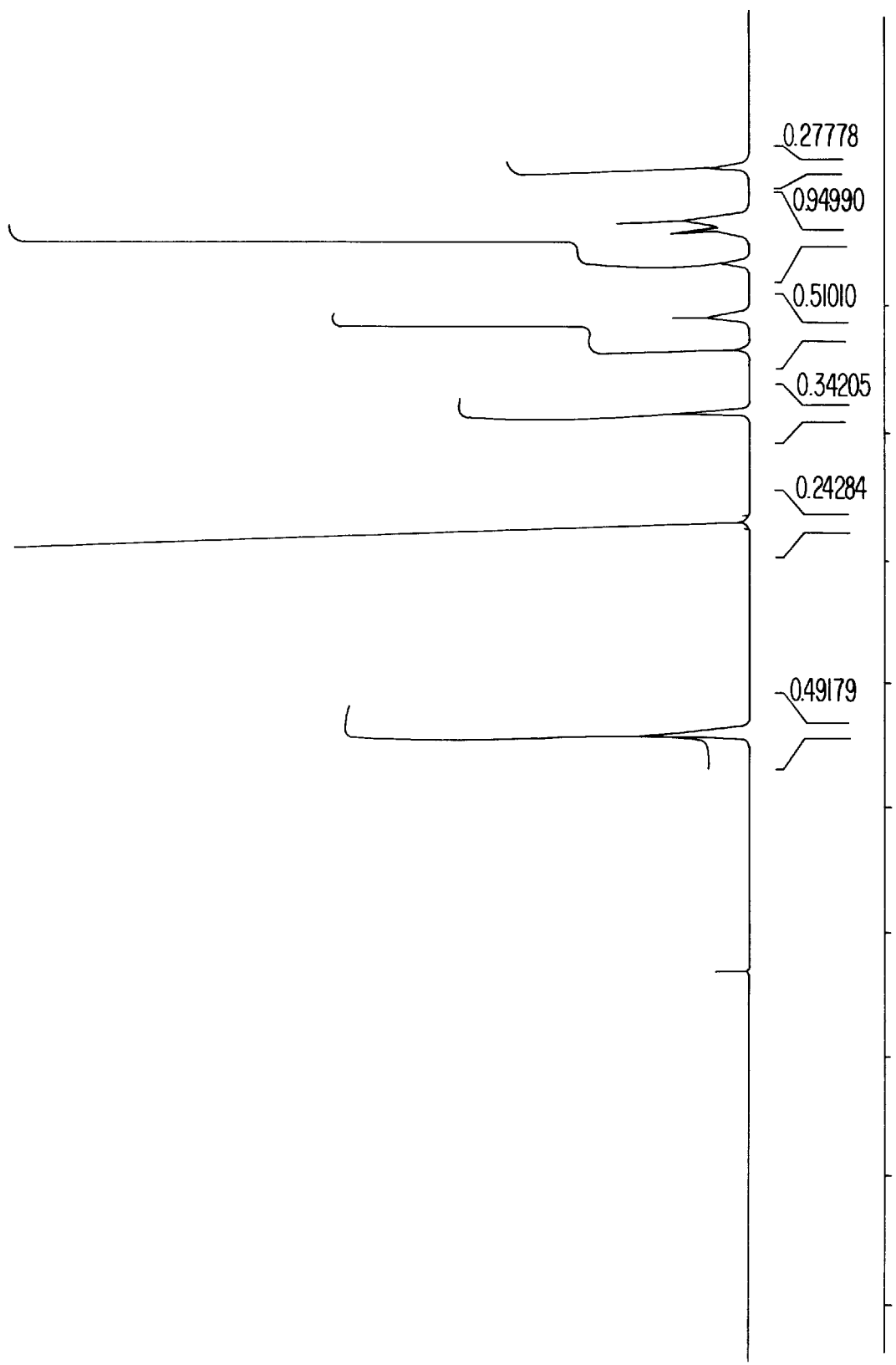
FIG. 1 is a NMR spectrum of methyl γ-linoleate at the time of preparation.

The examples below illustrate the invention without limiting its scope:

EXAMPLE I

1% Dispersion of Dihomo-γ-linolenic acid

| | |
|---|---|
| Dihomo-γ-linolenic acid | 1 g |
| Hydroxypropyl methylcellulose | 99 g |

The dihomo-γ-linolenic acid is dissolved in 10 ml of acetone at 0° under a nitrogen atmosphere. The solution thus obtained is gradually mixed with hydroxypropyl methylcellulose whilst maintaining the stream of nitrogen.

The paste formed is collected and dried under vacuum at the lowest possible temperature.

The powder is collected then mixed with lactose and talc to form 1000 tablets containing 1 mg of dihomo-γ-linolenic acid.

EXAMPLE II

2% Dispersion of Dihomo-γ-linolenic acid

| | |
|---|---|
| Dihomo-γ-linolenic acid | 2 g |
| Hydroxypropyl methylcellulose | 100 g |
| Wheat starch | 125 g |
| Lactose | 25 g |
| Magnesium stearate | 5 g | for 1000 finished tablets with a mean weight of 0.255 g and containing 2 mg of dihomo-γ-linolenic acid per tablet.

The dihomo-γ-linolenic acid is dissolved in 25 ml of acetonitrile freshly redistilled over an anti-oxidant and dehydrated by drying over magnesium sulphate, degassed beforehand by nitrogen bubbling. The organic solution thus obtained is filtered under nitrogen, added gradually to the hydroxypropyl methylcellulose, dried under vacuum then sieved to obtain a homogeneous powder. The mixture thus formed is added in turn to the wheat starch. The lactose is then added and, finally, the magnesium stearate. The final mixture is granulated, ground then sieved over a 200 sieve. The fine powder thus collected is compressed to form tablets with a mean weight of 0.255 g.

The dispersions of dihomo-γ-linolenic acid prepared according to Examples I and II are fully stable in storage. The loss after 2 years' storage at ordinary temperature is less than 0.4%. There is no trace of hydroxylated or ketonic derivative normally found in the product after degradation.

The unit dosage ranges from 0.2 mg to 1 mg of dihomo-γ-linolenic acid per test sample The daily dosage in humans ranges from 0.4 mg to 4 mg of dihomo-γ-linolenic acid divided or distributed in hydroxypropyl methylcellulose.

EXAMPLE III

Storage of an Adsorbate of γ-linolenic acid on Hydroxypropyl Methylcellulose

Introduction

The aim is to obtain a 1% dispersion (m/m) of γ-linolenic acid (abbreviated to GLA) in hydroxypropyl methylcellulose (HPMC).

Products

The polyunsaturated fatty acid was stored in the refrigerator. An NMR spectrum at 400 MHz of the proton confirms that the product has not undergone any deterioration during transport.

The hydroxyalkyl cellulose used is Methocel E3Prem. (Dow Chemical) (HPMC).

The stability of the mixture was first studied in the initial form, that is, non-adsorbed, at ambient temperature and under magnetic agitation. The product is analysed after dilution in acetone (1 to 2 mg in 1 ml of acetone) and determination by GC. The evaluation of the chromatograms shows that:

For the first two days, the stability of the non-adsorbed preparation is good.

On the third day, degradation products start to appear (96.6% residual).

On the fourth day, degradation continues (91% residual).

On the seventh day, degradation is considerable and, finally, after 15 days, there is no further trace of initial γ-linolenic acid. From the eighth day onwards, the product becomes opaque and yellowish. Its viscosity increases to a pasty state. The γ-linolenic acid diluted in acetone undergoes the same development.

Method of Operating for the Preparation of an Adsorbate

Using a syringe, a sample of 0.05 g of polyunsaturated fatty acid is taken and placed in a flat-bottom ground glass flask. The liquid is diluted with 2 g of analytical grade acetone, then 5 g of HPMC are dispersed manually in the solution. The dispersion is mixed for 10 mn with a Rotavapor under nitrogen. A. vacuum is applied and evaporation lasts for about 10 mn (absence of acetone odour). The product recovered is ground gently in a mortar in order to remove agglomerates. Finally, the powder (3.5 g) is placed in a penicillin flask and kept away from the light in a refrigerator.

Figure 2:
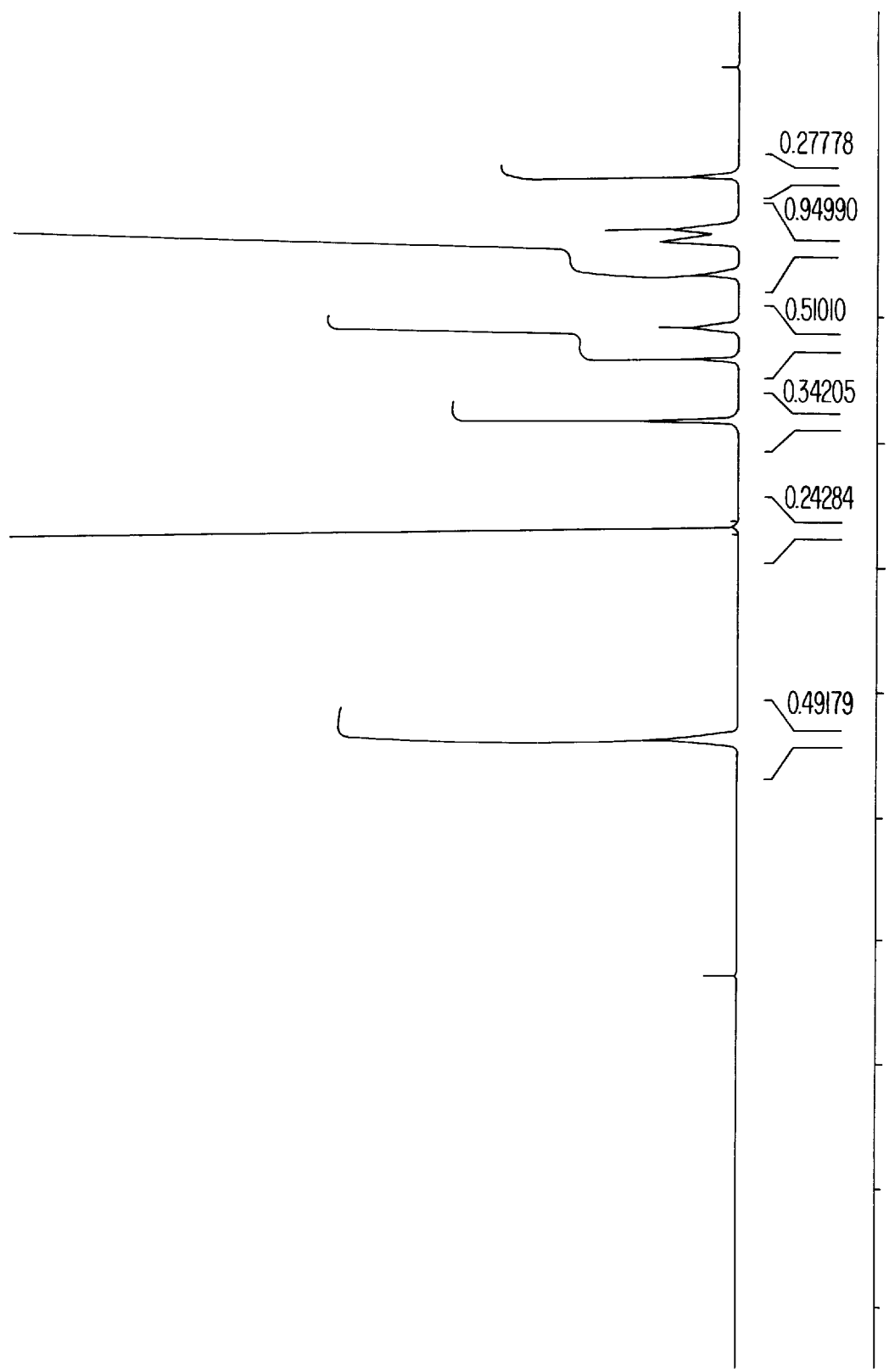
FIG. 2 is a NMA spectrum of the same product after 6 months storage and FIG. 3 is an enlargement of the spectrum of FIG. 2.
Figure 3:
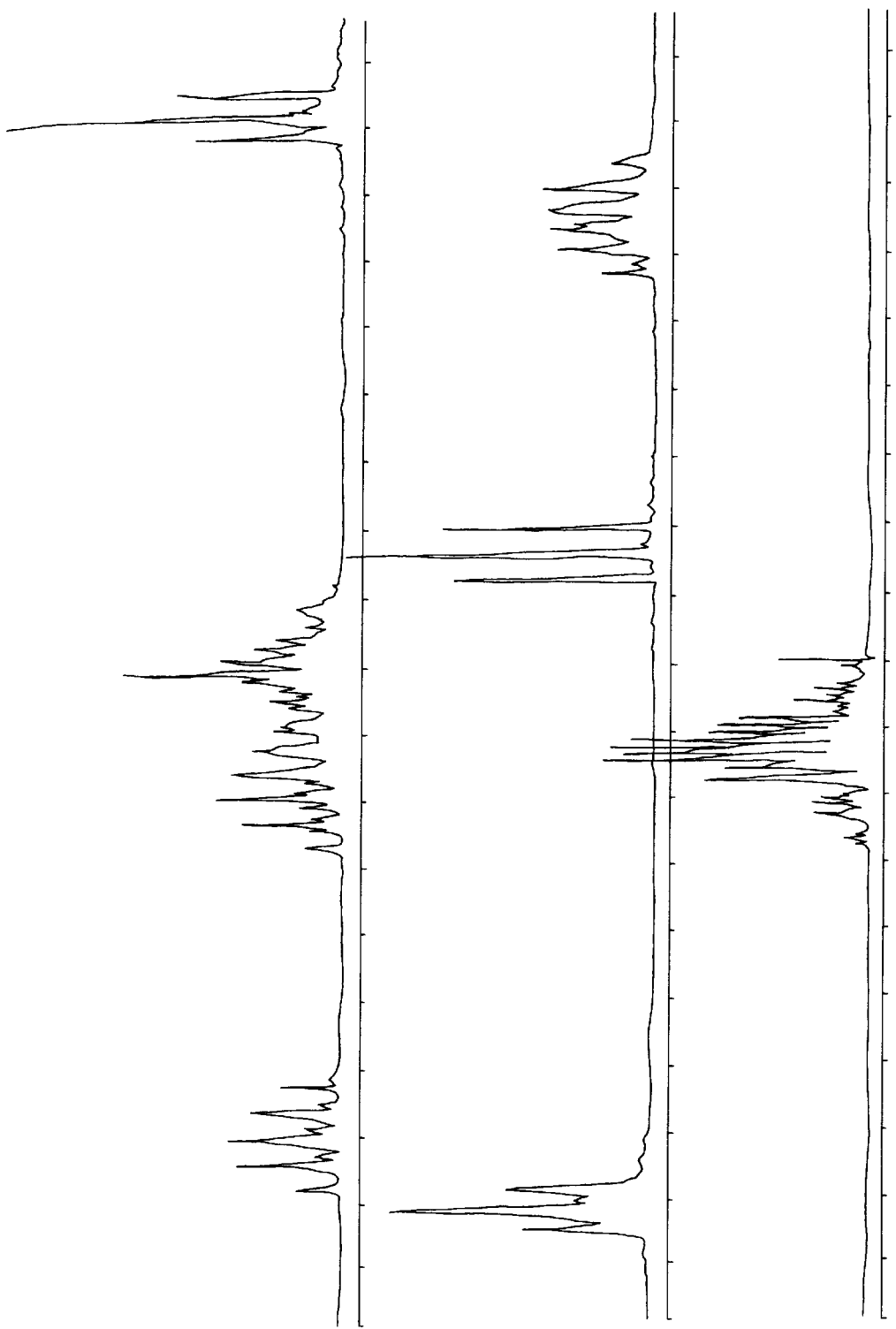
Figure 4:
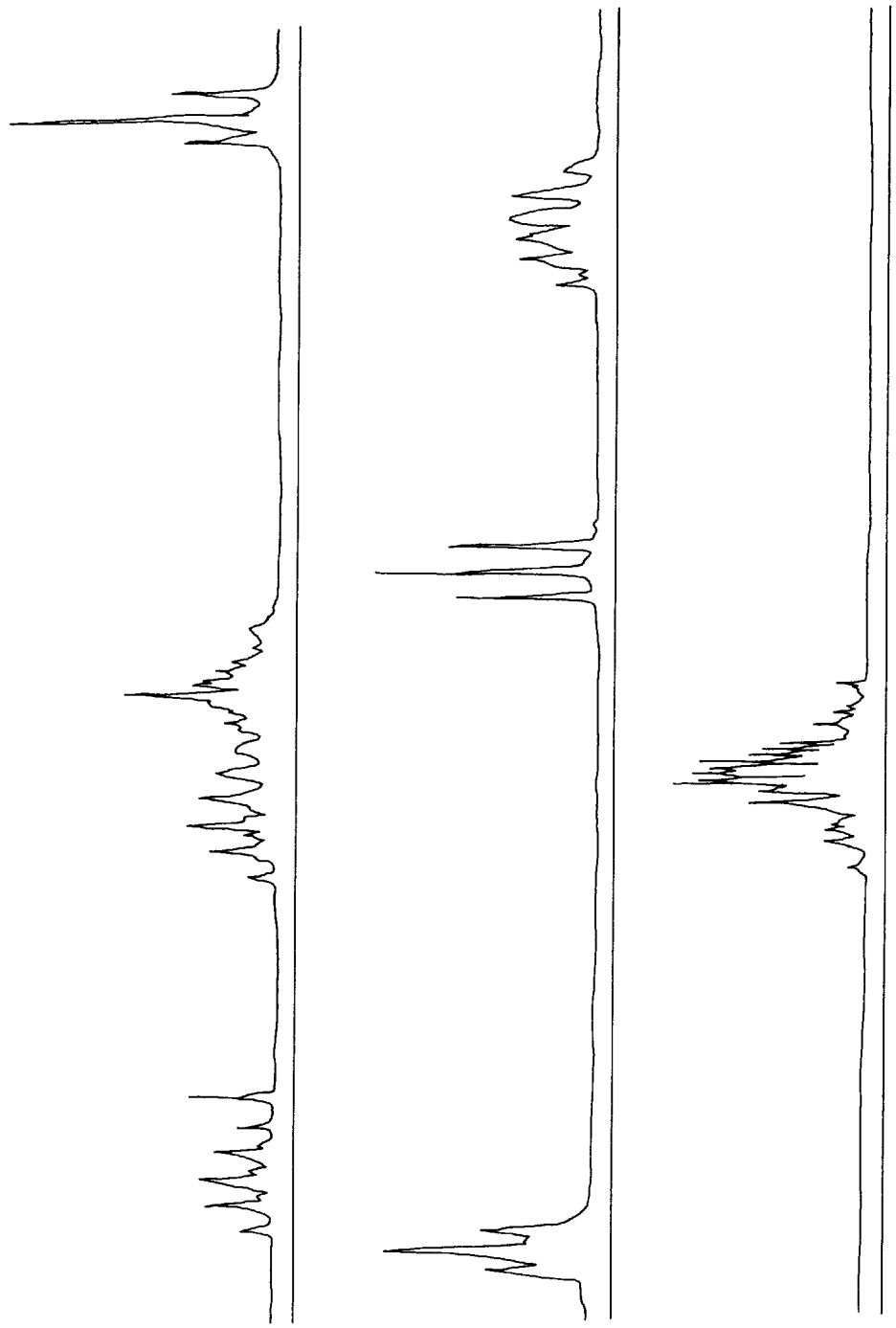
FIG. 4 is a comparison of the spectra of FIGS. 1 to 3.

The various tests carried out yield very similar results (the recent batch is even purer) and confirm the structure of the compound and its stability. The NMR spectra attached hereto show that the products have not undergone any deterioration over time. FIG. 1 is the spectrum of the methyl-γ-linolenate adsorbed, determined at the time of preparation, and FIG. 2 is the NMR spectrum of the same product after six months' storage at ambient temperature. FIG. 3 is an enlargement of the spectrum in FIG. 2.

Ageing of the Initial Product

The stability was studied on the liquid product in its original form at ambient temperature and under magnetic agitation. For the purpose of the analysis, the product is diluted in acetone (1 to 2 mg in 1 ml of acetone), and the product is then determined by GC coupled with MS and by NMR $^1$[H] or $^{13}$[C].

Macroscopically, the appearance of the powders is completely different. The unstabilised product, that is, simply dissolved in acetone at ambient temperature, assumes the appearance of an ochre-coloured paste.

I claim:

1. A process for the complete and prolonged stabilisation of polyunsaturated fatty acids or of one of their alkyl esters, characterised in that the polyunsaturated fatty acid or one of its alkyl or glyceryl esters is dissolved in an organic solvent, this solution is added to a hydroxyalkyl cellulose or to a solution thereof in an inert solvent, then the solution or dispersion thus obtained is evaporated to dryness under a protective gas atmosphere in order to form the preparation in powder form.

2. A stabilisation process according to claim 1, wherein the hydroxyalkyl cellulose is a hydroxyethyl or a hydroxypropyl cellulose.

3. A stabilisation process according to claim 1, wherein the hydroxyalkyl cellulose is a (hydroxyalkyl) alkyl cellulose.

4. A stabilisation process according to claim 1, wherein the hydroxyalkyl cellulose is a (hydroxypropyl) methylcellulose.

5. A process according to claim 1, wherein the organic solvent is a non-hydroxylated solvent.

6. A process according to claim 1, wherein the non-hydroxylated organic solvent is acetonitrile or acetone.

7. New pharmaceutical compositions characterised in that they contain a polyunsaturated fatty acid, one of its alkyl esters or one of its glyceryl esters adsorbed on a hydroxyalkyl cellulose, in association or in mixture with an inert, non-toxic excipient or vehicle which is pharmaceutically acceptable for oral or topical administration.

8. A pharmaceutical composition according to claim 7, wherein the weight ratio of polyunsaturated fatty acid/hydroxyalkyl cellulose ranges from 0.1 to 50%.

9. A pharmaceutical composition according to claim 7, wherein the weight ratio of polyunsaturated fatty acid/hydroxyalkyl cellulose ranges from 1 to 10%.

10. A pharmaceutical composition according to claim 7, wherein the unit dosage ranges from 0.2 mg to 1 mg of polyunsaturated fatty acid.

11. A pharmaceutical composition according to claim 7, wherein the polyunsaturated fatty acid is stearidonic acid.

12. A pharmaceutical composition according to claim 7, wherein the polyunsaturated fatty acid is α-linolenic acid.

13. A pharmaceutical composition according to claim 7, wherein the polyunsaturated fatty acid is dihomo-γ-linolenic acid.

14. A pharmaceutical composition according to claim 7, wherein the polyunsaturated fatty acid is γ-linolenic acid.

15. A pharmaceutical composition according to claim 7, wherein the polyunsaturated fatty acid ester is the triglyceride of γ-linolenic acid.

16. A pharmaceutical composition according to claim 7, wherein the polyunsaturated fatty acid is a semi-synthetic or synthetic analogue of dihomo-γ-linolenic acid (8, 11, 14-eicosatetraenoic acid) substituted in the 2, 3, 4, 5, 18 or 19 position.

17. A pharmaceutical composition according to claim 7, wherein the polyunsaturated fatty acid is 19-methyl 8, 11, 14-eicosatrienoic acid.

18. Cosmetic compositions for skin care characterised in that they contain a polyunsaturated fatty acid, one of its alkyl esters or one of its glyceryl esters adsorbed on a hydroxyalkyl cellulose, in association or in mixture with one or more inert carriers or vehicles suitable for application to the skin.

* * * * *